United States Patent [19]
Garti et al.

[11] Patent Number: 5,847,109
[45] Date of Patent: Dec. 8, 1998

[54] GALACTOMANNAN PRODUCTS AND COMPOSITIONS CONTAINING THE SAME

[75] Inventors: Nissim Garti; Abraham Aserin, both of Jerusalem; Zecharia Madar, Rehovot; Boaz Sternheim, Hatichon, all of Israel

[73] Assignee: Yissum Research Development Company, Israel

[21] Appl. No.: 693,188

[22] PCT Filed: Feb. 7, 1995

[86] PCT No.: PCT/GB95/00239

§ 371 Date: Nov. 19, 1996

§ 102(e) Date: Nov. 19, 1996

[87] PCT Pub. No.: WO95/21199

PCT Pub. Date: Aug. 10, 1995

[30] Foreign Application Priority Data

Feb. 7, 1994 [IL] Israel .................................... 108583

[51] Int. Cl.⁶ ............................. C08B 37/00; C07H 1/06; C07H 1/00; A61K 31/715
[52] U.S. Cl. ........................ 536/123; 536/123.1; 536/127; 536/128; 514/54
[58] Field of Search ................................... 536/123, 123.1, 536/128, 127; 514/54

[56] References Cited

PUBLICATIONS

Karawya et al, Planta Medical Journal of Medicinal Plant Research, vol. 38, No. 1, Jan. 1980, pp. 73–78, "Mucilogenous Contents of Certain Egyptian Plants".

Maier et al, Industrial Gums, Edited by Whistler et al., third edition, Academic Press, San Diego, pp. 218–221, "Guar, Locust Bean, Tara, and Fenugreek Gums", 1993.

*Primary Examiner*—John Kight
*Assistant Examiner*—Everett White
*Attorney, Agent, or Firm*—Townsend and Townsend and Crew LLP

[57] ABSTRACT

An isolated galactomannan having at least 50 repeating units of mannose and galactose in a ration of between 0.5–1.0 and 1.8–1.0, and having a protein content of less than 20 wt. %, a saponin content of less than 5 wt. %, and a lipid content of less than 1 wt. %, which can be used as an active ingredient in nutraceutical and cosmetic products.

8 Claims, 6 Drawing Sheets

FIG. 9
Average Insulin Changes

FIG. 10
Percent Change Glucose Levels

GALACTOMANNAN PRODUCTS AND COMPOSITIONS CONTAINING THE SAME

This application is a 371 of PCT/GB95/00239, filed Feb. 7, 1995.

The present invention relates to an isolated galactomannan and to comestible nutraceutical compositions and cosmetic compositions containing the same. More particularly, the present invention relates to comestible nutraceutical products and cosmetic products containing a specific and unique galactomannan as an active ingredient therein.

As will be described hereinafter, the galactomannans of the present invention have also been found to possess unique and unexpected emulsifying properties.

As is known, the seeds of many leguminous plants have mucilaginous endosperms [see, e.g., H. Meier and J. S. Grant Reid, "Morphological Aspects of Galactomannan Formation in the Endosperm of Trigonella Foenum-graecum Leguminosae," *Planta*, Vol. 133, pp. 243–248 (1977)]. The endosperms of many leguminous seeds contain galactomannans [P. Andrews, et al., "Mannose-Containing Polysaccharide, Part 2. The Galactomannan of Fenugreek Seed (Trigonella Foenum-graecum)," *J. Chem. Soc.*, p. 2744–2750 (1952); and J. S. Grant Reid and H. Meier, "Formation of Reserve Galactomannan in the Seed of Trigonella Foenum-graecum," *Phytochemistry*, Vol. 9, pp. 513–520 (1970)]. The proportion of D-galactose to D-mannose in the polysaccharide varies from species to species and possibly within species [P. M. Dey, "Biochemistry of Plant Galactomannans," *Adv. Carbohydr. Biochem.*, Vol. 35, pp. 341–376 (1978)]. The galactomannans, with one reported exception [E. L. Hirst and J. K. N. Jones, "The Galactomannan of Carob-Seed (Gum-Gatto)," *J. Chem. Soc.*, pp. 1278–1280 (1948)], have a common basic structure. To the chains of β-1-4-D-mannopyranosyl residues (polymannose-M) are attached, at the 6-position, single D-galactopyranosyl residues (galactose-G). The galactomannans from the seeds of different species differ with respect to their ratios of galactose to mannose residues. Small differences in the proportion of galactose to mannose residues in galactomannans from plants of the same species have been reported by different groups of workers, and it has been suggested that this may be due to varietal or environmental factors [I. C. M. Dea and A. Morrison, "Chemistry and Interactions of Seed Galactomannans," *Adv. Carbohydr. Biochem.*, Vol. 31, pp. 241–312 (1975)].

The most important property of galactomannans is their high water binding capacity and the formation of very viscous solutions at relatively high dilutions. The galactose side chains cause extension of the very long mannan chains and keep them from forming hydrogen bonded insoluble associates (pure linear polymannan is completely water insoluble). Guar gum, with a high galactose content, swells and dissolves readily in cold water, whereas carob bean gum (LBG) needs heating to dissolve [H. Neukom, "Galactomannan: Properties and Applications," *Lebensemwiss U. Technol.*, Vol. 22, pp. 41–45 (1989)]. The solubility of tara gum is intermediate, as can be expected from the galactose content.

Like other hydrocolloids, the galactomannans are insoluble in organic solvents. They can be precipitated from aqueous solution by addition of water-miscible solvents, such as ethyl alcohol.

The galactomannans are important viscosity builders. They exhibit non-Newtonian behavior, in which the viscosity decreases with the shear rate. The solutions show no viscosity change upon aging (30 days) at room temperature, only slight viscosity decrease on the addition of electrolytes, and no viscosity change at pH range of 3 to 7.

The galactomannans are mainly used when an efficient thickening or stabilizing effect is needed. Thick, stable and smooth solutions are obtained in high dilution, which make the galactomannans very economical to use [M. Glicksman, "Comparative Properties of Hydrocolloids: Functional Properties," In: *Food Hydrocolloids*, Vol. 1, CRC Press, Inc., Florida, U.S.A., pp. 47–59 (1982)].

In many food applications, the galactomannans are used in the presence of oils or fats, and are called "stabilizing agents." Salad dressings are good examples of such systems. The role of the galactomannans in these foods is not simply that of a thickening agent, and seems to be more complicated.

Fenugreek (Trigonella Foenum-graecum) is a less-known galactomannan than guar gum or LBG. It is both more water-soluble and a less efficient thickening agent than either of said well-known gums. The ability of fenugreek gum as a stabilizer and thickener has not previously been disclosed and practically had not been studied, although the structure of the galactomannan of fenugreek has been well-documented. It has galactose and mannose residues in the ratio of 1:1 or, in a few cases, of 1:2 [N. W. Alcock, et al., "Stereochemistry of the 4-hydroxy-iso-leucine from Trigonella Foenum-Graecum," *Phytochemistry*, Vol. 28, pp. 1835–1841 (1989)].

Wide-angle X-ray diffraction of the hydrated fenugreek shows that the polysaccharides crystallize as an orthorhombic lattice, with a=9.12A; b=33.35A; and c=10.35A. The density is consistent with four chains passing through the unit cell. The fundamental crystal structure is very similar to other galactomannans except for the b dimension, which is slightly larger than in guar [B. K. Song, et al., "Crystallography of Highly Substituted Galactomannans: Fenugreek and Lucerne Gums," *Macromolecules*, Vol. 2 2, pp. 2641–2644 (1989)].

Fenugreek seeds, ground into a powder, are known for their health benefits with regard to reduction of cholesterol [R. D. Sharma, et al., "Effect of Fenugreek Seed on Blood Glucose and Serum Lipids in Type 1 Diabetes," *European J. of Clin. Nutr.*, Vol. 44, pp. 301–306 (1990)] and sugar levels in the blood stream.

According to the present invention, it has now been surprisingly found that, upon proper isolation of the active ingredients of the seeds, the polysaccharide part of the seeds (hereinafter referred to as "fenugreek galactomannan") reduces surface tension to values (42 dyne/cm) lower than guar gum (55 dyne/cm). The interfacial activity of fenugreek galactomannans was also surprisingly better than that of other galactomannans (interfacial tension was reduced to 2 dyne/cm in vegetable oils), which led to the formation of oil-in-water emulsions with small droplet size (2–3 microns) and long-term stability. The fenugreek gum was found to adsorb (or "Precipitate") on the oil interface, forming a relatively thick interfacial film. Emulsions formed with fenugreek galactomannans as the emulsifying agent are more stable than any equivalent emulsions stabilized by other galactomannan gums. No flocculation was observed in emulsions stabilized with fenugreek concentrations sufficient for a good coverage of the oil interface.

It has further been found that commercial crude seeds of fenugreek, af ter undergoing extraction and concentration to reduce their protein, saponin and lipid contents (such a galactomannan being referred to hereinafter as "isolated galactomannan") possess unexpected and unique properties as a nutraceutical agent, which properties are not possessed by commercial galactomannans. The term "nutraceutical" as used herein is now recognized in the art as referring to nutrition and food products, usually from natural sources, having some pharmaceutical benefits.

With regard to the isolated galactomannans described hereinafter, it has been surprisingly found that they reduce post-prandial glucose and insulin response, as well as cholesterol levels.

The isolated galactomannans of the present invention also possess unique emulsifying properties, and therefore can be included in comestible products not only as a nutraceutical agent, but also as an emulsifying agent.

Furthermore, the isolated galactomannans of the present invention, due to their emulsifying properties, can be used in cosmetics as a carrier for sustained slow release of other components, selected, e.g., from lipids and steriods, such as cholesterol to be slowly delivered to the skin surface.

In addition, the isolated galactomannans of the present invention have been found to be effective in preventing constipation and in regulating bowel movement in mammals, and can be used to manufacture both veterinary and pharmaceutical compositions by methods known per se, using accepted additives, carriers and diluents.

Based on these discoveries, the present invention provides an isolated galactomannan having at least 50 repeating units of mannose and galactose in a ratio of between 0.5–1.0 and 1.8–1.0, and having a protein content of less than 20 wt %, a saponin content of less than 5 wt. %, and a lipid content of less than 1 wt. %.

In preferred embodiments of the present invention, said isolated galactomannan has a protein content of less than 15 wt. %, a saponin content of less than 2 wt. %, and a lipid content of less than 0.1 wt. %.

Preferably, the ratio of mannose and galactose in said isolated galactomannan is primarily 1:1, and said isolated galactomannan is derived from fenugreek.

In preferred embodiments of the present invention, there is provided a comestible nutraceutical product comprising galactomannan, primarily of the repeating formula I:

wherein n is greater than 100, as a nutraceutical agent therein.

The comestible nutraceutical products of the present invention can include desserts, ice creams, puddings, and jellies incorporating the isolated galactomannans according to the present invention, as well as soups and beverages. In addition, the isolated galactomannans can be provided in comestible powder or tablet form, with or without other per se known additives, carriers, fillers and diluents.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

EXAMPLE 1

Materials and Methods

Isolation of the Hydrocolloid

Dry seeds of fenugreek were purchased from the local market. The source was Trigonella foenum-graecum, grown in India. The seeds (125 gr) were ground to fine powder (300 mesh) and extracted by the Soxhlet procedure in the presence of 2×100 ml n-hexane for 5 hr. to colourless solution. The n-hexane solution that contained most of the lipids (1.5 g) was discarded. The solid fraction was further extracted with methanol (200 ml), followed by ethanol (150 ml). The extract was vacuum-evaporated and lyophilized to yield 7–8 g of a mixture of saponins. The remaining solids were further treated and dissolved in water (800–1000 ml), to form a viscous aqueous solution of crude fenugreek gums. The extraction process was repeated four times. The water-soluble fractions were combined and the hydrocolloid fractions were precipitated by adding ethanol at 1:1 weight ratio.

The precipitated fenugreek gum (20 wt. % of the solid crude seeds) was lyophilized to obtain a dry mass that could be easily ground to a fine powder. The isolated fenugreek galactomannan produced was measured as having a protein content of between 8–10%, a saponin content of less than 0.5%, and a lipid content of less than 0.05%.

Further Purification of the Gum

Fenugreek crude solution (0.1 wt. % with 6 wt. % proteins) was percolated through a Florusil column (150 mm length×25 mm diameter) of 200 mesh, with double distilled water. After the purification process, the samples contained 1 wt. % so-called tripurified protein. The analysis was done with bicinchoninic acid, using the BCA method of Pierce International. Each of the obtained samples: purified, bipurified, and tripurified, were tested for their surface activity.

Surface and Interfacial Tensions

Surface and interfacial tensions were measured at a controlled temperature bath (25° C.) by the Wilhelmy technique, using a platinum plate (Lauda Tensiometer, Germany) and the results and fenugreek gum concentrations were plotted against time until equilibrium was reached. Samples were equilibrated up to 12 hours.

Results

Rheological Properties

Figure 1:
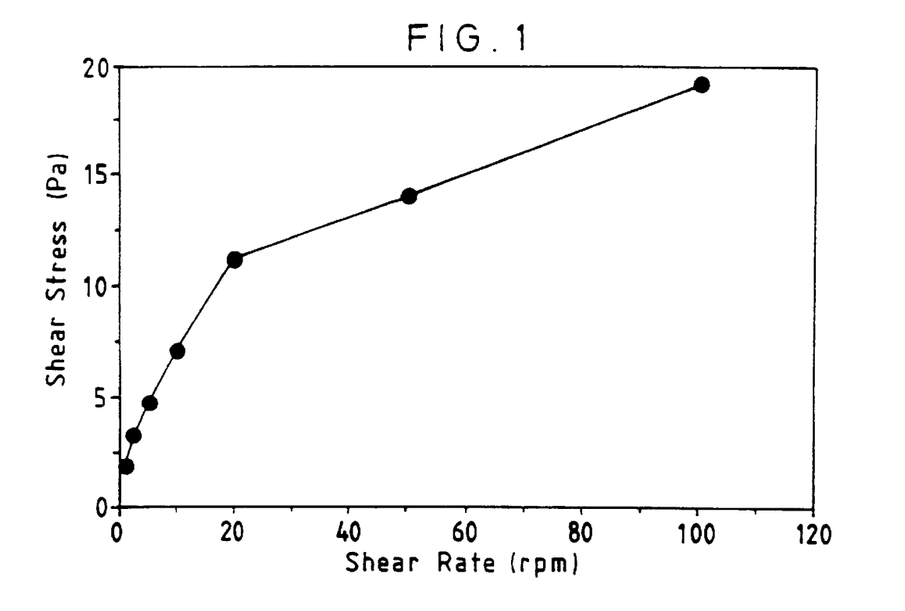
FIG. 1 is a plot of shear stress vs. shear rate (rpm) for fenugreek bipurified gum solutions of 0.7 wt. % at 25° C.
Figure 2:
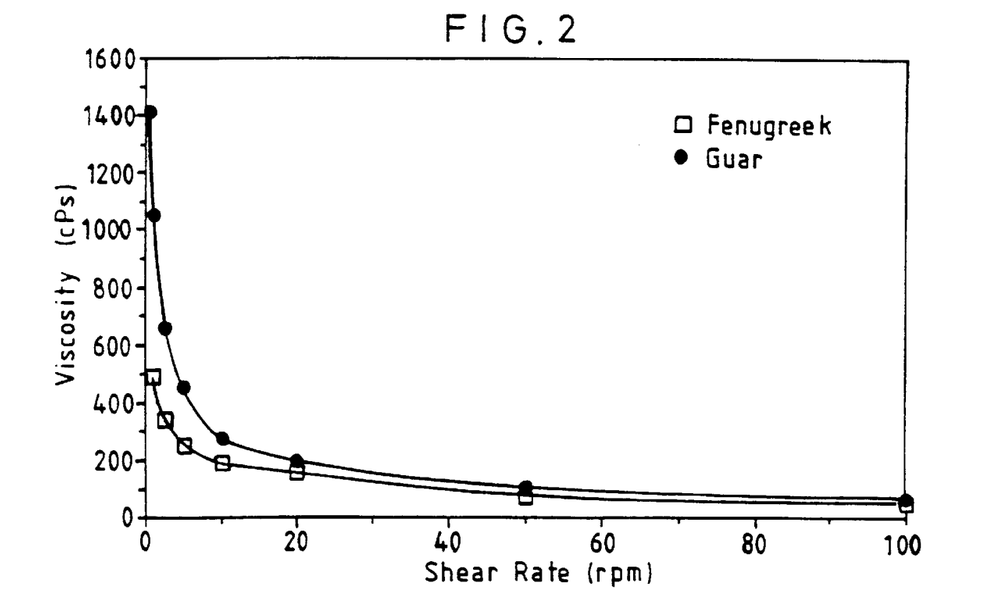
FIG. 2 is a plot of viscosity (cPs) vs. shear rate for 0.7 wt. % solutions of bipurified fenugreek gum and guar gum.

Viscosity measurements of the bipurified fenugreek gum solution reveal, as expected, that the gum has non-Newtonian properties: the viscosity is reduced with the temperature and the shear rate. A plot of the shear stress vs. the shear rate exhibits a typical curve (FIG. 1). A comparison between the viscosity behavior of guar gum and fenugreek at 0.7 wt. % is presented in FIG. 2. The results indicate that the viscosity of the guar solution is slightly higher than that of the fenugreek solution, mainly at the low shear rates. This effect was expected, in view of the fact that the fenugreek gum is highly substituted by galactose units on the mannan backbone. Galactomannans do not form gels unless they interact with other gums, such as xanthan or k-carrageenan gum. Attempts were made to form gels with fenugreek gum in the presence of k-carrageenan gum; however, they were unsuccessful.

Surface Properties

Figure 3:
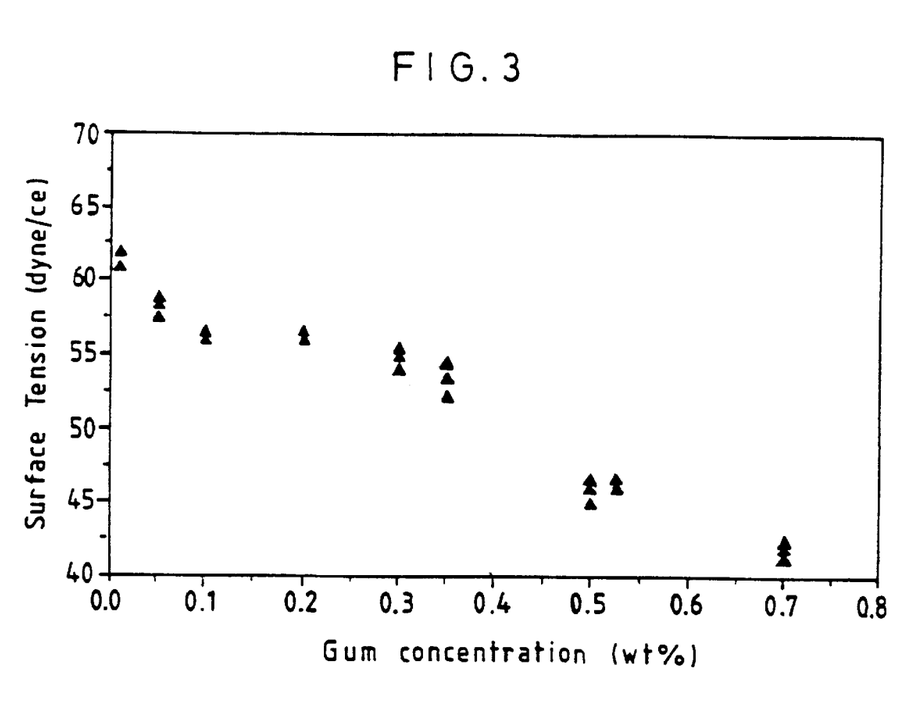
FIG. 3 depicts the surface tensions (dyne/cm) of bipurified fenugreek gum aqueous solution as a function of gum concentration.

The polysaccharide hydrocolloids are mostly hydrophilic polymers, water-soluble and rigid, and therefore are not expected to exhibit significant surface activity. However, guar and LBG were found to migrate slowly to the water-air and water-oil interfaces and exhibit some emulsification activities [D. Reichman, Ph.D. Thesis, "Characterization of Hydrocolloids—Surface Activity and Interactions with Monomeric Emulsifier at the Interface," The Hebrew University of Jerusalem, Israel (1992)]. The bipurified fenugreek gum was also tested for its surface properties and found to be more efficient in lowering the interfacial free energy. It can reduce the surface tension of water to 42 dyne/cm at 0.7 wt. % (see FIG. 3) in comparison with 55 dyne/cm at 0.7 wt. % for guar gum. The fenugreek gum is more efficient than gum arabic (60 dyne/cm at 1 wt. %) or xanthan gum (42 dyne/cm at 1 wt. %) [D. Reichman and N. Garti, ibid. (1991)]. The curve seems to be composed of three different forms, depending on gum concentration. At very low gum concentrations (up to 0.1 wt. %), the surface tension reduction was probably due to the adsorption of short chain saccharides, which can migrate preferentially to the surface. The second part (0.1 to 0.5 wt. %) probably corresponds to the behavior of macromolecules at the surface. Non-reproducible measurements were obtained for gum concentrations above 0.9 wt. %, because of the buildup of a high viscosity in the solution.

It has been well-documented that the surface activity of gum arabic is attributed to the protein, which is chemically bound to the polysaccharide [D. M. W. Anderson, "The Amino Acid Composition and Quantitative Sugar-Amino Acid Relationships in Sequential Smith-Degradation Products from Acacia Polyacantha Gum," Food Addit. Contam., Vol. 3, pp. 123–132 (1986)]. All the native commercial galactomannans are contaminated with 5–10 wt. % proteins. In previous studies, the present inventors have shown that guar can be purified to reduce its protein levels to 0.8 wt. %, without affecting its surface properties. The native fenugreek gum is contaminated with proteinous components at levels of 6 wt. % (based on nitrogen analysis and a 6.25 factor). The fenugreek gum was further purified to eliminate as much as possible of the proteins associated with the polysaccharides.

Table I demonstrates the differences in viscosity, surface tension and interfacial tension of fenugreek gum solutions after purification (6 wt. % protein), after centrifugation (bipurified, 2 wt. % protein), and after column purification (tripurified, 0.85 wt. % protein).

TABLE 1

Physical and surface properties of purified fenugreek (6 wt. % protein) in comparison to bipurified gum (2 wt. % protein) and tripurified column purification (0.85 wt. % protein)

| Fenugreek gum | Protein (wt %) | Viscosity (cPs) | $\gamma o$ (dyne/cm) | $\gamma i$ (dyne/cm) | Ave droplet size (microns) |
|---|---|---|---|---|---|
| Purified | 6.0 | 350 | 42 | 26 | 3 |
| Bipurified | 2.0 | 250 | 42 | 20 | 2 |
| Tripurified | 0.85 | — | 40 | 19 | 2.5 |
| Heat treated | 6.0 | — | 42 | 26 | 3 |

*O/W emulsion 5% oil 0.5% Gum.

The intrinsic viscosity of the bipurified solution was slightly decreased, compared to the purified gum. The surface activity was slightly improved (40 dyne/cm for tripurified gum; 42 dyne/cm for bipurified solution, and 46 dyne/cm for the purified gum solution). Similar improvement was detected for the n-tetradecane/water interfacial tension (20 dyne/cm for the bipurified, vs. 19 dyne/cm for the tripurified).

In order to test the activity of the remaining protein (which could still be considered an associated/bound protein) in the bipurified fraction, the powdered gum and the gum solution were preheated for 2 hr at 60° C. (see Table 1, above). No significant difference in the gum behavior could be detected. The experiments suggest that either (1) the associated proteinaceous polymers are not affected (not denatured) by the heating process; (2) the protein has no significant role as surfactant; or (3) the protein is not chemically attached to the polysaccharide. Any additional attempts to further solvent-purify the gum failed.

Our experimental work shows clearly that the fenugreek gum is not affected by the protein concentration present therein as an impurity.

It was therefore concluded that the proteinaceous matter does not have any significant effect on the surface activity of the fenugreek gum. This conclusion may draw criticism from the scientific community, in view of the fact that other gums lost their activity upon removal of protein from the native gum [E. Dickinson, et al., "Emulsifying Behavior of Acacia Gums," in: Gums and Stabilizers for the Food Industry, Vol. 5, G. O. Phillips, D. J. Wedlock and P. A. Williams, Eds., IRL Press, Oxford, England, pp. 41–44

(1990); J. Benjamins, et al., "Dynamic and Static Properties of Proteins Adsorbed at the Air/Water Interface," *Farady Discuss. Chem. Soc.*, Vol. 59, pp. 218–229 (1975); and A. G. Goankar, "Surface and Interfacial Activities and Emulsion Characteristics of Some Food Hydrocolloids," *Food Hydrocolloids*, Vol. 5, pp. 329–337 (1989)].

Figure 4:
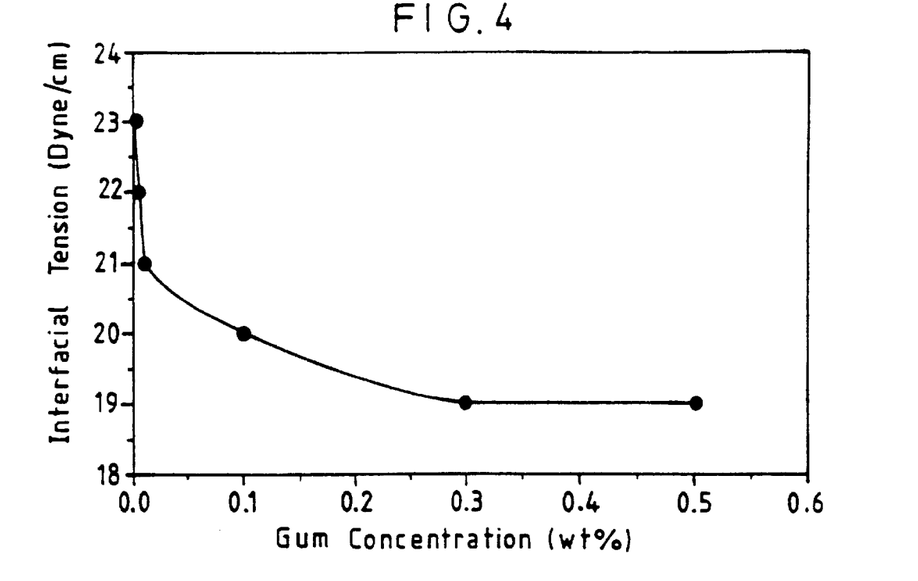
FIG. 4 shows the interfacial tensions (dyne/cm) of n-tetradecane-water in the presence of bipurified fenugreek gum.

The interfacial tensions between oils/water were reduced to quite remarkable values at levels of 0.1 to 0.5 wt. % of fenugreek solution. FIG. 4 demonstrates the reduction of the interfacial tension between n-tetradecane and water as a function of the gum concentration. The lowest value was found to be 19 dyne/cm, in comparison to 27 dyne/cm for guar gum. The interfacial tensions of toluene (36 dyne/cm), soybean oil (24 dyne/cm) and castor oil (16 dyne/cm), were reduced to 7, 3.5 and 2 dyne/cm, respectively. For any of the oils, the fenugreek gum effect on the interfacial tension was greater than that of guar gum.

Emulsification Activity

Figure 5:
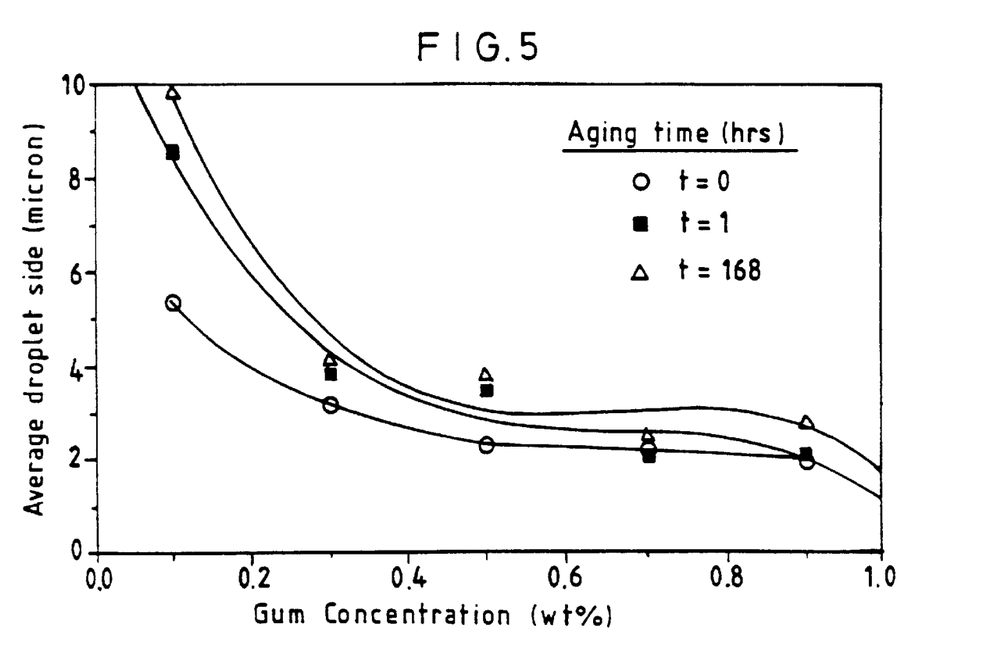
FIG. 5 shows the average droplet size of 5 wt. % n-tetradecane-in-water emulsion, stabilized with fenugreek gum as emulsifier.
Figure 6:
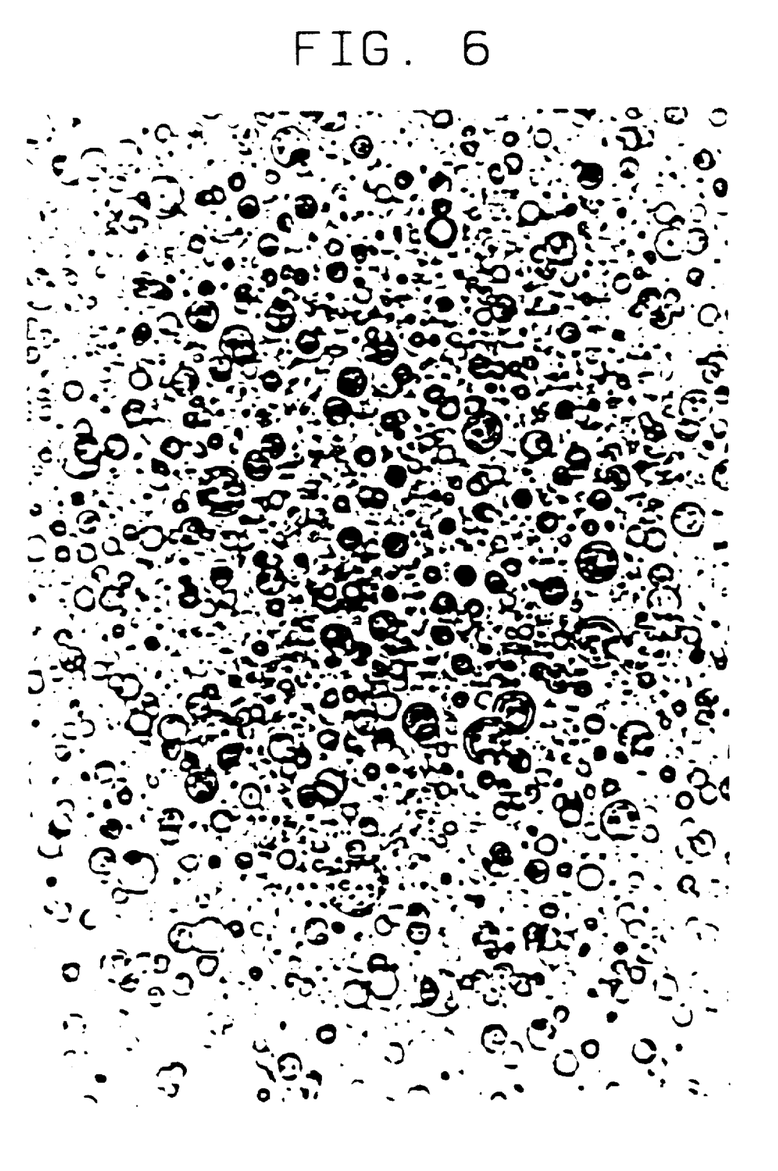
FIG. 6 depicts typical droplets of 5 wt. % n-tetradecane-in-water emulsions prepared with 0.9 wt. % fenugreek gum after homogenization with ultraturrax and microfluidizer (1 cm eq 2.5 $\mu$m)

Oil-in-water emulsions (5 wt. % oil) were prepared in the presence of 0.1–0.9 wt. % bipurified gum. High shear rates (microfluidizer) were applied to obtain good emulsification. The droplets were found to be significantly smaller than those obtained from guar gum (FIG. 5). Plot of the average droplet size as a function of the fenugreek gum concentration and storage time reveals that, at low gum concentrations (partial droplets coverage), the droplets are large and tend to coalsce quickly with time. The increase in the gum concentration, at the same oil levels, allows better coverage of the droplets, resulting in the formation of smaller droplets with only a minor tendency to coalesce. At levels of 0.9 wt. %, the droplets are small (3 microns) and do not exhibit flocculation or coalescence (FIG. 6). The droplet size distribution was plotted as a function of the gum/oil ratio (termed $R_c$) (normalized gum to oil concentration) to obtain the ratio for which the oil coverage was optimal. Most stable emulsions were formed. It can be demonstrated that, at gum/oil x100 values of ($R_c$>12), the emulsions were stable and free of flocculation for a long time. The oil to gum critical ratio required to obtain efficient droplet coverage, $R_c$, was compared to other galactomannans and found to be smaller, reflecting more efficient interfacial coverage (20, 18 and 12 for LBG, guar and fenugreek gums, respectively). It was therefore concluded that the fenugreek is more efficient than the other galactomannans in stabilizing oil-in-water emulsions.

Figure 7:
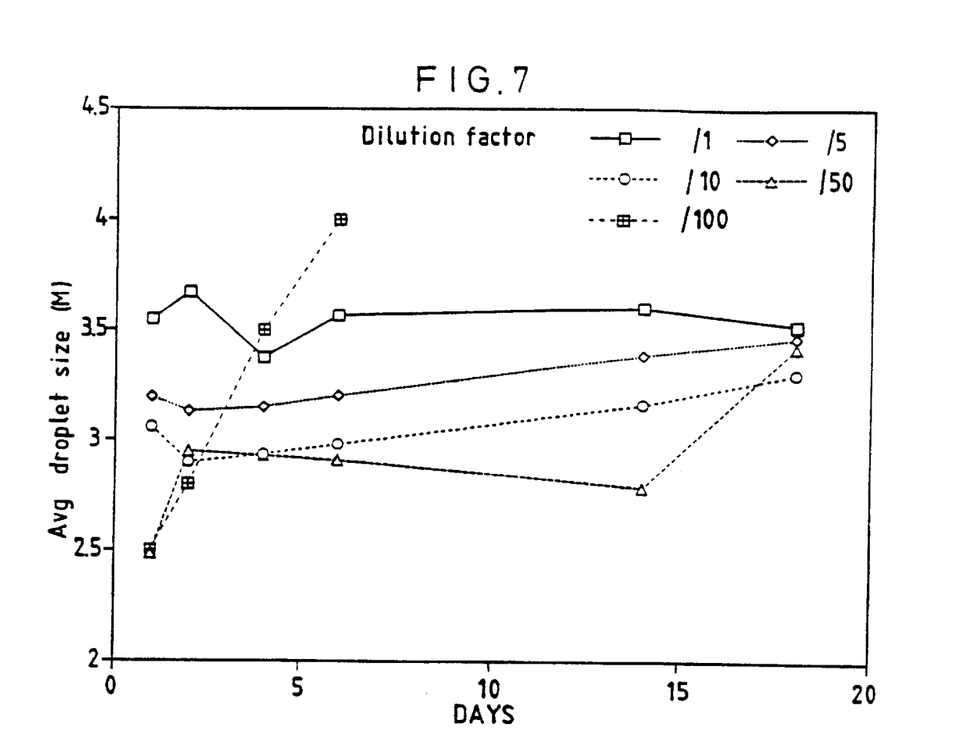
FIG. 7 shows the average droplet size against aging time of 5 wt. % n-tetradecane-in-water emulsion, stabilised with 0.7 wt. % gum, and diluted up to 1,000-fold.

In order to evaluate the adsorption efficiency of the fenugreek gum on the oil droplets, the 5 wt. % tetradecane-in-water emulsions, prepared with 0.7 wt. % gum ($R_c$=14), were further diluted up to 1000, and the droplet size distribution was measured against aging time (FIG. 7). It can be seen that only strong dilution affects the average droplet size, indicating that gum desorbs from the interface. This indicates that gum is weakly adsorbed/precipitated on the oil interface.

Figure 8:
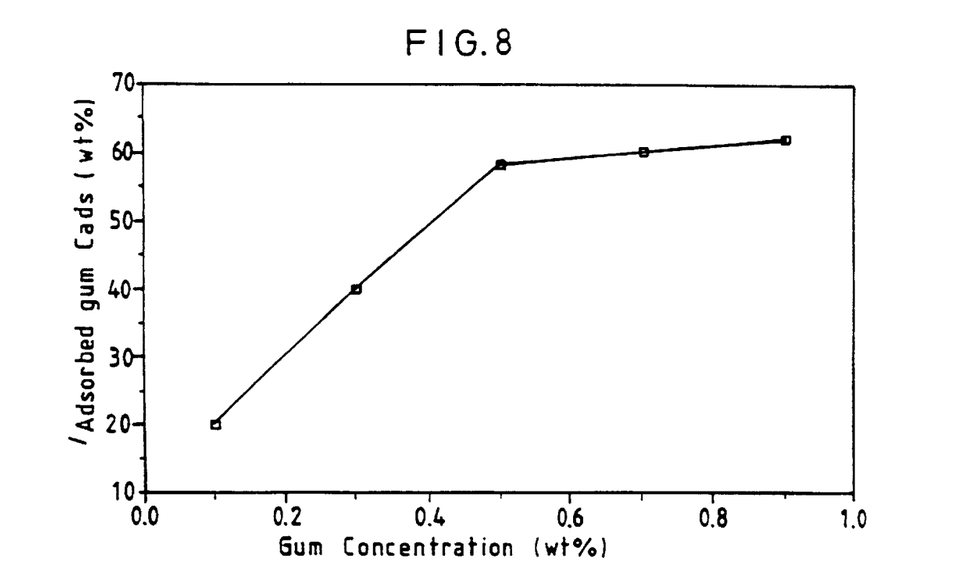
FIG. 8 is a plot of the amount of fenugreek adsorbed (wt. %) on the n-tetradecane droplets, as a function of gum concentration in the emulsification process (oil phase was 10 wt. %)

The interfacial gum concentration was estimated from these sets of experiments, in which the gum concentration varied from 0.1 to 0.7 wt. %. The percentage of gum in the emulsifier phase, which in fact reflects the concentration of the gum adsorbed ($C_{ads}$), was calculated as a function of the total gum concentration for any oil fraction. It was demonstrated that the gum adsorbs onto the oil interface, and its efficiency is remarkable, reaching a maximum of 60 wt. % of the added gum at 10 wt. % oil and 0.7 wt. % gum (FIG. 8). The gum coverage efficiency is indicated to be better than other galactomannans in which $R_c$=18 [D. Reichman and N. Garti, "Hydrocolloids of Food Emulsifiers and Stabilizers," *Food Structure* (submitted, 1993)], and very similar to some surface-active proteins.

EXAMPLE 2

Fenugreek-derived galactomannan produced according to Example 1 was tested to determine the effect thereof on post-prandial glucose and insulin levels in a cross-over study.

Twenty-two subjects, eleven of whom were diabetics of at most ten-year duration, and the remaining eleven of whom were obese individuals at least 20% above ideal body weight, were divided into two groups, each consisting of five or six persons who were diabetics and five or six who were obese. Each group had baseline measurements of glycohemoglobin, glucose and insulin. They were all then fed a low-fiber, high-carbohydrate breakfast of bagel and rice cereal. One group received, blended into their breakfast, 10 g of fenugreek-derived galactomannan, while the second group did not.

In addition to baseline levels, 20 cc of blood were drawn at 60, 90, 120, and 180 minutes after breakfast. The initial 60-minute blood was tested for glucose and insulin. At all other times, only glucose was tested.

One week later, the procedure was repeated, with the groups crossing over.

The quantity chosen to represent the reaction was the integral of the curves depicting the change from the initial time in glucose levels versus time. For insulin, where only the initial and one-hourly values were available, the designated quantity was simply the hourly change in insulin levels. The change in insulin concentrations indicates the reaction to the ingestion of the carbohydrate-laden meal.

The integrals were computed using the trapezoidal rule for numerical integration. This means averaging the end points of the increment and multiplying by the length of the increment. For the 0, 60, 90, 120 and 180 min. points, the value at 0 min. was always 0, because the curves were for changes from the initial conditions. The integral (normalized to hours) over the full interval then involved computing 0.5 $(3_{a1}+2_{a2}+3_{a3}+3_{a3}+2_{a4})$, where a is the value of the variable, and the subscripts 1, 2, 3, 4 refer to times 60, 90, 120 and 180, respectively.

Results

Figure 9:
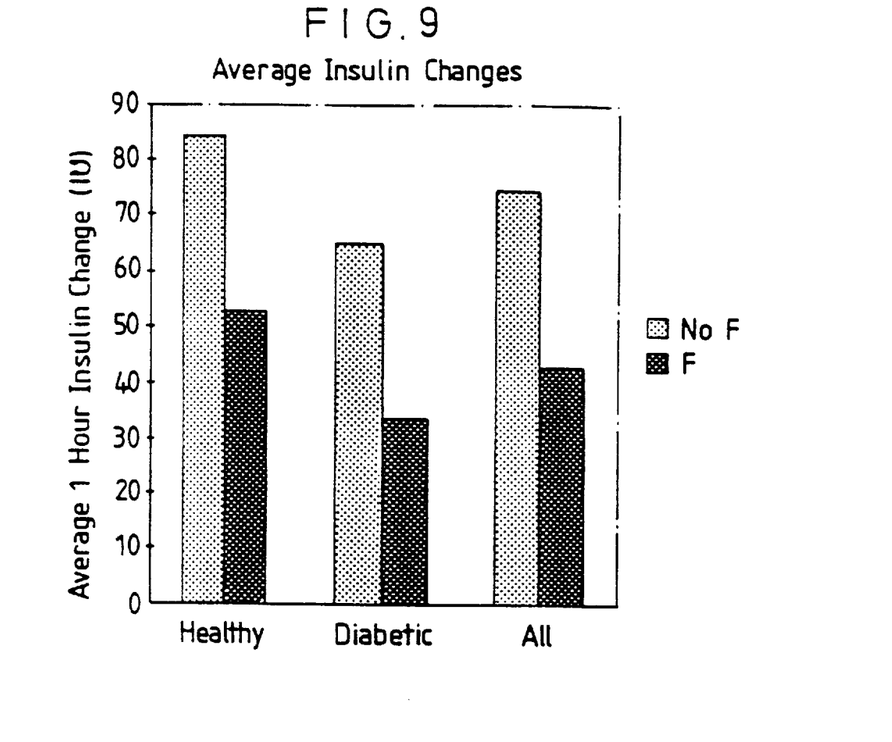
FIG. 9 is a graph showing a comparison of average one-hour changes in insulin levels for healthy, diabetic, and combined subjects, with and without fenugreek-derived galactomannan.

The one hour insuling change showed the most dramatic response to the fenugreek-derived galactomannan in all subjects. FIG. 9 compares the changes in blood insulin concentrations with and without the ingestion of fenugreek-derived galactomannans, averaged among healthy, diabetic, and all subjects combined. As can be seen, the fenugreek-derived galactomannan diminished the insulin response among all subjects. The percent decrease for healthy subjects was 37.62; for diabetics, 48.26; and for all combined 42.51. These results were all statistically significant (P-values (two-tailed) for healthy subjects, 0.003; for diabetics, 0.013; and for total, 0.008).

Figure 10:
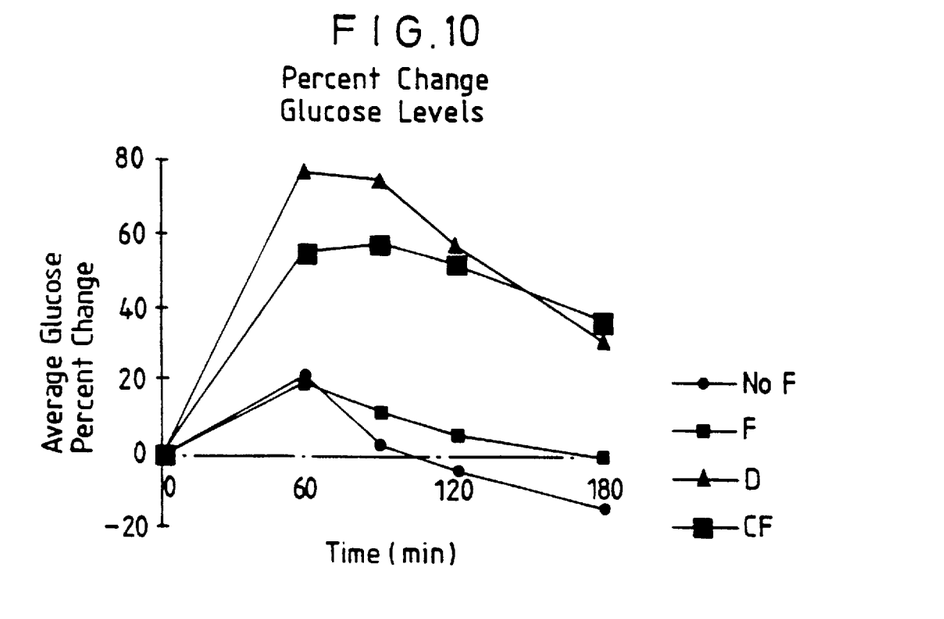
FIG. 10 is a graph showing the average percent change in glucose concentrations versus time, with and without fenugreek-derived galactomannan, for healthy and diabetic subjects.

FIG. 10 shows the average percent change in glucose from the initial time, for diabetics and healthy subjects, with and without fenugreek-derived galactomannan. For the healthy obese, there was no significant difference in the integrals between subjects with and without fenugreek-derived galactomannan (two-tailed p-value=0.153). In the diabetics, on the other hand, the glucose increase is significantly decreased for the galactomannan-receiving group in comparison with the non-receiving group (two-tailed p-value=0.025).

Discussion

It is clear that in both diabetics and healthy obese, fenugreek-derived galactomannan had an impact on the insulin response, and in diabetics, on the post-prandial glucose tolerance as well. In most cases, however, the effect of the galactomannan was to "flatten the curve." That is to say, the fenugreek-derived galactomannan seemed to restrain the larger fluctuations. This includes the tendency of some of the healthy subjects to over-react to the intake of carbohydrates and produce a hypoglycemic downturn of glucose levels. FIG. 10 clearly demonstrates that the healthy subjects on average suffered a hypoglycemic reaction, which could be due only to an overly-stimulated pancreas. The consumption of fenugreek-derived galactomannans seems to slow this reaction, by either blocking some of the glucose absorption outright, or by slowing it down. Indeed, many of the subjects who had consumed fenugreek-derived galactomannan volunteered that they felt "full" or "bloated" for many hours following breakfast. This may be due to the slower metabolism of the glucose in these individuals and may constitute an unanticipated beneficial side effect of the fenugreek-derived galactomannan consumption.

EXAMPLE 3

Fenugreek-derived galactomannan produced according to Example 1 was compared with other common fibers and dietary supplements for reducing post-prandial glucose absorption and insulin response in Type II diabetics, obese subjects, and healthy controls.

Example 3 was intended to compare the results of Example 2 with results from other dietary supplements, and to determine the response variability with respect to subject and dosage. The experiment was conducted on approximately 200 individuals.

Example 3 tested the efficacy of fenugreek-derived galactomannan against a variety of dietary supplements, including oat bran, apple pectin, soy flour, amaranth flour, glucomannan, psyllium, guar gum, and other commercially available flours or fibers. The subjects participated as much as three mornings per week, for up to two months, but no more frequently than once every 48 hours. Subjects had an initial blood drawing to determine baseline values of glucose and insulin. They were then fed a 500 Kcal metabolic breakfast, consisting of bagel, cream cheese or peanut butter, coffee, and apple sauce. On various days, 1–20 g of fenugreek-derived galactomannan, or any of the other dietary supplements, alone or in various combinations, was mixed into the apple sauce. It is important to stress that all the dietary supplements being used, including the fenugreek-derived galactomannan, are generally recognized as safe.

A subsequent blood sample was drawn one hour after breakfast. All blood drawings were approximately 10 cc. Initial and one-hour levels of glucose and insulin were measured. Changes in insulin and glucose functioned as a guide to the efficiency of each of the fibers in the blocking of glucose absorption, as well as an indication as to the optimal dosage of fenugreek-derived galactomannans.

EXAMPLE 4

Dry seeds of fenugreek were purchased from the local market. The source was Trigonella foenum-graecum, grown in India. The seeds (125 gr) were ground to fine powder (300 mesh). 100 g of the powder were then combined with 1000 g water and the mixture was heated to a temperature of between 80°–90° C. and maintained at said temperature for an hour and a half. The resulting liquid was separated into liquid and solid phases by centrifugation at a speed of 2500 rpm for 10 minutes.

The liquid phase was then combined with ethanol at a ratio of about 1:0.75 alcohol, which resulted in the precipitation of the desired gum product. The precipitate was separated and then dried at a temperature of 50° C.

The resulting isolated fenugreek galactomannan gum product was found to have a protein content of 10–14%, a saponin content of less than 1%, and a lipid content of less than 0.05%.

EXAMPLE 5

Dry seeds of fenugreek were purchased from the local market. The source was Trigonella foenum-graecum, grown in India. The seeds (125 gr) were crushed and introduced into a solvent having a specific gravity in the range of between 1.25 and 1.35, selected from $CH_2Cl_2$, $CHCl_3$, and $CCl_4$. The gum component of the outer coating of the seeds sank to the bottom while the kernels floated, thereby allowing separation and further processing of the fenugreek without the kernel component thereof. The procedure of Example 4 was then followed.

The resulting isolated fenugreek galactomannan gum product was found to have a protein content of 2–6%, a saponin content of less than 0.1%, and a lipid content of less than 0.05%.

As will be realized, utilizing the difference in specific gravity between the undesired kernel component of the seeds and the desired gum-containing outer coating of the seeds, it is possible to devise other methods of separation, including mechanical separation by a fluidized bed air flow. This type of pre-separation step before processing has the advantage of reducing the volume of undesired components, and results in an inherent saving in processing costs.

It will be evident to those skilled in the art that the invention is not limited to the details of the foregoing illustrative examples, and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An emulsified isolated fenugreek galactomannan having at least 50 repeating units of mannose and galactose in a ratio of between 0.5–1.0 and 1.8–1.0, and consisting essentially of isolated hydrocolloid galactomannan fractions in combination with impurities selected from the group consisting of a protein content of less than 20 wt. %, a saponin content of less than 5 wt. % a lipid content of less than 1 wt. % and mixtures thereof, said galactomannan being present in an amount of up to 0.7 wt. % of the total emulsion.

2. An emulsified isolated fenugreek galactomannan according to claim 1, wherein said galactomannan has a protein content of less than 15 wt. %, a saponin content of less than 2 wt. %, and a lipid content of less than 0.1 wt. %.

3. An emulsified isolated fenugreek galactomannan according to claim 1, wherein a major portion of the mannose and galactose units therein are in a ratio of 1:1.

4. An emulsified isolated fenugreek galactomannan according to claim 1, comprising galactomannan primarily of the repeating formula I:

wherein n is greater than 100.

5. An emulsified isolated fenugreek galactomannan according to any of claims 1 to 4 for use as a comestible nutraceutical product.

6. An emulsified fenugreek galactomannan for use as a nutraceutical product according to claim 5, wherein said use is effective in reducing post-prandial glucose, insulin response and cholesterol levels.

7. An emulsified isolated fenugreek galactomannan according to claim 5 for use as a cosmetic product.

8. An emulsified isolated fenugreek galactomannan according to claim 7, for use as a cosmetic product, wherein said isolated fenugreek galactomannan acts as a sustained slow release carrier for component selected from the group consisting of lipids and steroids.

* * * * *